(12) United States Patent
Renard-Le Galloudec et al.

(10) Patent No.: US 7,555,102 B1
(45) Date of Patent: Jun. 30, 2009

(54) SYSTEMS AND METHODS FOR IMAGING USING RADIATION FROM LASER PRODUCED PLASMAS

(76) Inventors: Nathalie Renard-Le Galloudec, 5625 Fox Ave., Reno, NV (US) 89506; Thomas E. Cowan, 2220 Schooner Cir., Reno, NV (US) 89509; Yasuhiko Sentoku, 1790 Omellaia Way, Reno, NV (US) 89521; Jennifer Rassuchine, 845 Rhode Island Dr., Reno, NV (US) 89503

(*) Notice: Subject to any disclaimer, the term of this patent is extended or adjusted under 35 U.S.C. 154(b) by 36 days.

(21) Appl. No.: 11/732,920

(22) Filed: Apr. 5, 2007

Related U.S. Application Data

(60) Provisional application No. 60/789,841, filed on Apr. 5, 2006.

(51) Int. Cl.
  H01J 35/08 (2006.01)
  H05G 1/00 (2006.01)
(52) U.S. Cl. .................................. 378/143; 378/124
(58) Field of Classification Search ............. 378/119, 378/124, 140, 143
  See application file for complete search history.

(56) References Cited

U.S. PATENT DOCUMENTS

| | | | |
|---|---|---|---|
| 5,010,562 A * | 4/1991 | Hernandez et al. ........ 378/125 |
| 5,471,516 A * | 11/1995 | Nunan ..................... 378/65 |
| 5,787,146 A | 7/1998 | Giebeler | |
| 6,275,565 B1 * | 8/2001 | Tomie ..................... 378/119 |
| 6,332,017 B1 | 12/2001 | Carroll et al. | |
| 6,594,335 B2 | 7/2003 | Davidson | |
| 7,200,203 B2 * | 4/2007 | Cocks et al. ............. 378/119 |
| 2001/0038680 A1 | 11/2001 | Davidson | |
| 2007/0019789 A1 | 1/2007 | Bloom | |

FOREIGN PATENT DOCUMENTS

WO    2007/033060 A1    3/2007

OTHER PUBLICATIONS

Adams, et al., "Cone Fabrication," *Nanomechanics University of Nevada*, Reno 1-6, Oct. 19, 2004.
Adams, et al., "Hemisphere Fabrication," *Nanomechanics University of Nevada*, Reno 1-4, Oct. 19, 2004.
Baldelli, et al., "Quasi-monochromatic x-rays for diagnostic radiology," *Physics in Medicine and Biology* 48 3653-3665, 2003.

(Continued)

*Primary Examiner*—Edward J Glick
*Assistant Examiner*—Thomas R Artman
(74) *Attorney, Agent, or Firm*—University of Nevada, Reno / DRI Technology Transfer Office; Ryan A. Heck

(57) ABSTRACT

In particular embodiments, the present disclosure provides systems and methods for imaging a subject using radiation emitted from a laser produced plasma generating by irradiating a target with a laser. In particular examples, the target includes at least one radiation enhancing component, such as a fluor, cap, or wire. In further examples, the target has a metal layer and an internal surface defining an internal apex, the internal apex of less than about 15 μm, such as less than about 1 μm. The targets may take a variety of shapes, including cones, pyramids, and hemispheres. Certain aspects of the present disclosure provide improved imaging of a subject, such as improved medical images of a radiation dose than typical conventional methods and systems.

20 Claims, 10 Drawing Sheets

OTHER PUBLICATIONS

"Chirped pulse amplification," 5p., downloaded from http://en.wikipedia.org/w/index.php?title=Chirped_pulse_amplificati... on Mar. 28, 2007.

Cowan, "US-Japan Workshop on Fast Ignition," 1-4, Nov. 17, 2004.

Cowan, et al., "X-ray Imaging Spectroscopy of Ti Foils and Pyramidal Targets," 1, 2005.

Ditmire, "Fusion Science Center Research at UT: Hot electron and x-ray generation from cone shaped targets," *FI FSC Progress Meeting*, 1-25, Jun. 1, 2005.

De Donnea, "Conclusions of the Fusion Fast Track Experts Meeting," 1-5, Dec. 5, 2001.

Duvvuri, et al., "Spectroscopic Characterization of X-rays from Laser Produced Plasmas: Medical Applications," 1-28, Dec. 13, 2005.

Dyer, et al., "Pyramidal targets as an advanced radiation source in laser-solid interactions," *2005 Quantum Electronics and Laser Science Conference* 1804-1806, 2005.

European Fusion Development Agreement, "Cleaner Energy for the future," 1-8.

Fuchs, et al., "Demande de temps 2004 au LULI installation 100 TW," 1-12, 2004.

Fuchs, et al., "Demande de temps laser 2005 sur l'installation 100 TW dans le cadre du programme national d'accès aux installations du LULI," 1-5, 2005.

Galloudec, et al., "Developments of laser targets and operations of the target fabrication laboratory," 1-4, 2005.

Galloudec, et al., "Enhanced radiation sources with pyramidal target," 1, 2005.

Grätz, et al., "Time-gated x-ray tomography," *Applied Physics Letters* 73(20):2899-2901, Nov. 16, 1998.

Herrlin, et al., "Generation of X Rays for Medical Imaging by High-Power Lasers: Preliminary Results," *Radiology* 189 65-68, Oct. 1993.

Ichalalene, et al., "Image Quality Analysis for Dual Energy Subtraction Imaging With a Femtosecond Laser-Based Hard X-Ray Source," *IEEE Journal of Selected Topics in Quantum Electronics*, 7(6):912-917, Nov./Dec. 2001.

"Image: Chirped pulse amplification.png," 2p., downloaded from http://en.wikipedia.org/w/index.php?title=Image:Chirped_pulse_ampli... on Mar. 28, 2007.

Key, et al., "Fast Ignition: Physics Progress in the US Fusion Energy Program and Prospects for Achieving Ignition," 1-11, 2002.

Knelp, et al., "K-spectroscopy and x-ray yield optimization of microshaped targets," 1, 2005.

Krol, et al., "Laser-based microfocused x-ray source for mammography: Feasibility study," *Medical Physics* 24(5): 725-732, 1997.

Landen, et al., "X-ray backlighting for the National Ignition Facility," *Review of Scientific Instruments* 72(1): 627-634, Jan. 2001.

Lazos, et al., "An integrated research tool for X-ray imaging simulation," *Computer Methods and Programs in Biomedicine* 70:241-251, 2003.

"New Targets for Inertial," 5 p., downloaded from http://www.llnl.gov/str/November01/Tabak.html on Apr. 9, 2007.

Park, et al., "High Energy K(alpha) Radiography Using High-intensity, Short-pulse Lasers," *Physics of Plasmas* 1-37, Nov. 29, 2005.

Princeton Instruments, "High-Performance X-Ray Imaging Solutions," 1-16, 2004.

Rassuchine, et al., "The Production of Ultrafast Bright K-alpha X-rays from Laser Produced Plasmas for Medical Imaging," 1-2, 2005.

Reich, et al., "Yield Optimization and Time Structure of Femtosecond Laser Plasma K $\alpha$ Sources," *Physical Review Letters* 84(21):4846-4849, May 22, 2000.

Rousse, et al., "Efficient K $\alpha$ x-ray source from femtosecond laser-produced plasmas," *Physical Review* 50(30): 2200-2207, Sep. 1994.

Sentoku, et al., "Laser light and hot electron micro focusing using a conical target," *Physics of Plasmas* 11(6): 3083-3087, Jun. 2004.

Sjögren, et al., "High-repetition-rate, hard x-ray radiation from a laser-produced plasma: Photon yield and application considerations," *Review of Scientific Instruments* 74(4):2300-2311, Apr. 2003.

Svanberg, "Some applications of ultrashort laser pulses in biology and medicine," *Measurement Science Technology* 12:1777-1783, 2001.

Tanaka, et. al., "Basic and integrated studies for fast ignition," *Physics of Plasmas* 10(5): 1925-1930, May 2003.

"Ti-sapphire laser," 3p., downloaded from http://en.wikipedia.org/w/index.php?title-Ti-sapphire_laser&printabl... on Mar. 28, 2007.

Toth, et al., "In-line phase-contrast imaging with laser-based hard x-ray source," *Review of Scientific Instruments* 76:083701-01-083701-06, 2005.

Yu, et al., "High Magnification Imaging with a Laser-Based Hard X-Ray Source," *IEEE Journal of Selected Topics in Quantum Electronics* 5(4):911-915, Jul./Aug. 1999.

\* cited by examiner

SYSTEMS AND METHODS FOR IMAGING USING RADIATION FROM LASER PRODUCED PLASMAS

CROSS REFERENCE TO RELATED APPLICATIONS

This application claims the benefit of, and incorporates by reference, U.S. Provisional Patent Application No. 60/789,841 filed Apr. 5, 2006.

STATEMENT OF GOVERNMENT SUPPORT

This invention was made with United States Government support under grants DE-FC52-01NV14050, and DE-FC52-06NA27616 awarded by the National Nuclear Security Administration of the U.S. Department of Energy. The United States Government has certain rights in the invention.

TECHNICAL FIELD

The present disclosure relates to targets and their methods of fabrication. In particular examples, the present disclosure provides methods of fabricating metal targets useable as laser targets in high-energy laser-physics.

BACKGROUND

Current medical imaging techniques typically employ standard X-ray tubes. However, such X-ray tubes can pose several limitations on image quality including large focal spot, broad spectral range, inadequate output and long radiation duration.

The diagnostic range of X-rays in medicine typically requires energies from 10-100 keV. A major problem with typical current X-ray emission techniques in medicine is the broadband energy spectrum that contributes to patient dose while not improving the resulting image.

The interaction of a short-pulse, ultra-intense laser with a solid produces hot, dense plasmas, referred to as laser produced plasmas (LPPs). Heating of the target ionizes the surface layer resulting in suprathermal electrons. Some of these electrons are accelerated forward and penetrate into the unperturbed portion of the target. The resulting K-shell ionization leads to the emission of K-alpha X-rays.

While x-ray energy depends on the target material, total X-ray yield and energy spectrum are influenced by laser intensity, contrast and pulse duration as well as target thickness and geometry. LPP X-rays sources typically have a small source size due to the rapid heating of the target. Furthermore, the, typically, picosecond duration of the X-ray emission coupled with a high repetition rate laser can produce a high fluence of X-rays in a very short period of time.

Metal covered targets are used in some high energy physics applications, such as inertial confinement fusion. In some cases, such targets are shot with a laser in order to generate plasmas or high energy radiation.

Targets commonly used with lasers to produce plasma and radiation can suffer from several disadvantages. For example, conventional targets are often produced by micro-machining processes that typically produce targets having a tip sharpness, or apex dimensions, of 25 µm or larger. For example, an existing process involves micro-machining a mandrel, electroplating the mandrel with a desired metal, and then etching away the mandrel. Other processes involve depositing a metal layer on a plastic mold and then melting away the plastic mold. Some prior experiments have used metal coated silicon targets. However, the silicon included in such targets typically interferes with energy focusing and radiation enhancement.

The tips of targets produced by such processes can be significantly larger than the wavelength of the laser light that will be used with the target and therefore may not produce optimal energy. Similarly, the apexes, or tips, of the targets can be larger than the focal size (or spot size) of the laser, which can minimize any enhancements that might otherwise be conferred by the target shape.

In addition, such targets are typically manufactured individually and thus can be comparatively expensive. The expense of the targets may limit the number of targets available for use, thus potentially limiting how the targets can be used. For example, a limited number of targets available for a series of experiments may limit the quality or quantity of data obtained during the experiments.

The amount of material available on such targets, or irregularities in the target surface, may interfere with full characterization of the produced plasma. Insufficient target material may also interfere with optimal energy production.

While hemispherical laser targets have been tested, such targets typically suffer from disadvantages in addition to those noted above. For example, irregularities in the surface of the target, or variations in the targets resulting from their method of manufacture, may make it difficult to properly position the target and position other objects with respect to the target.

SUMMARY

Particular embodiments of the present disclosure provide imaging methods. According to one implementation, k-alpha x-rays are produced by irradiating a target with a laser. The targets are hollow and have a metal layer. The targets may have straight or curved surfaces, or a combination thereof. In more specific examples, the hollow targets have an internal apex of less than about 15 µm, such as less than about 10 µm. In specific examples, the internal apex is less than about 1 µm. Particular disclosed target shapes include cone shaped targets, pyramidal targets, and hemispherical targets. In particular embodiments, the metal targets are free-standing. In further embodiments, the targets are arranged in arrays. Some disclosed targets are surrounded by a protective frame or a structure that aids in manipulating the targets.

In particular implementations, the new targets produce an enhanced x-ray yield or energy profile which can provide improved imaging applications. In particular examples, the enhanced x-ray yield results from increased hot electron density. In further embodiments, the disclosed targets can enhance K-alpha emission. In a more particular example, the enhanced K-alpha emission results from increased hot electron density. Particular target embodiments focus hot electrons along an internal surface towards the apex, such as by having a conical shape.

In further embodiments, the disclosed targets include at least one radiation enhancing component, such as an embedded fluor, a wire extending from the target apex, an additional layer on the exterior of the target, or have a cap perpendicular to the apex. In more specific examples, the target includes a plurality of such components. In particular examples, the fluor is located at the focal point of the target. The fluor, wire, layer, or cap can act as an X-ray source and can be selected to provide a desired K-alpha energy. The use of a fluor, wire, layer, or cap can, along with the target itself, provide multiple types of radiation for imaging methods. The fluor, wire, layer, or cap can be made from one or more materials, which can be the same or different from the material or materials used in the target. In more specific examples, the targets have an internal apex of less than about 15 μm, such as less than about 1 μm.

The present disclosure also provides imaging systems. In a particular embodiment, the imaging system includes a laser, a hollow target as described above, and a detector configured to detect the radiation passing through a sample. In specific examples, the sample is a biological sample. The systems, in specific implementations, can include additional components, such as a target changer, focusing optics, an exit slit for radiation produced by the target, and a sample holder. In yet further implementations the system includes an additional laser for irradiating the target, such as to irradiate a fluor, wire, or cap of the target.

Laser-produced plasma (LPP) X-ray sources using hollow metal targets can improve imaging capabilities, such as by providing a compact, ultra-fast, or bright K-alpha X-ray source. In certain methods, the k-alpha radiation produced by the LPP has a relatively narrow bandwidth. X-ray source size also typically plays an important role in medical imaging, such as by limiting object magnification and resolution, two components in delineating structures.

In particular embodiments, the energy of the LPP is tailored such that lower energies (which would be primarily scattered and absorbed in tissue) and the higher energies (too penetrating to hold any attenuation information) are limited, allowing the energy spectra to be tailored for a specific diagnostic purpose. Providing a greater amount of diagnostically useful radiation can enhance data quality or reduce patient exposure compared to irradiation with broader spectrum radiation. For example, narrow irradiation may reduce the dose of radiation a patient receives and allow lower radiation fluxes to be used. Similarly, using higher energy, or higher fluxes, of diagnostically useful radiation can increase data quality, such as by allowing for deeper penetration of radiation or enhanced signal to noise for a particular measurement. It also can be beneficial to augment photon flux in order to minimize both anatomical and physical motion of a patient and increase image quality.

The disclosed systems can be used in a number of imaging applications, including high magnification radiography. When the target is suitably positioned from the detector, such as when Fresnel conditions are obtained, the systems can be used for phase-contrast imaging by comparing real and imaginary components of x-ray transmission. Further methods employ time-gated imaging in order to enhance obtained images. Image algebra, such as image subtraction, is also used in some embodiments to enhance images.

Particular disclosed systems can be used in backlighting imaging experiments. For example, a layer of the material and a radiation generating components, such as a cap, fluor, additional exterior layer on the target, or wire, can be used to produce radiation having different characteristics. In further examples, the target includes a plurality of radiation generating components which can generate radiation having different characteristics. In various embodiments, such targets can be used in area backlighting, point projection backlighting using point targets, or point projection backlighting using pinholes. Compared to prior techniques, the present disclosure can be advantageous by allowing multiple types of radiation having different characteristics to be generated from a single target, in at least some embodiments using a single laser. The radiation generating components can be selected to provide desired types of radiation for a particular imaging technique, thus allowing the target to be tuned for a desired application.

In further embodiments, targets with a radiation enhancing component, or multiple radiation enhancing components are used to create a plurality of images. Image algebra, such as subtraction, can be used to produce composite images potentially having greater contrast for viewing particular features of the imaged object. In more particular examples, the image objected is treated with a radiosensitive material, such as administering a radiosensitive contrast agent, in order to enhance this contrast.

There are additional features and advantages of the subject matter described herein. They will become apparent as this specification proceeds.

In this regard, it is to be understood that this is a brief summary of varying aspects of the subject matter described herein. The various features described in this section and below for various embodiments may be used in combination or separately. Any particular embodiment need not provide all features noted above, nor solve all problems or address all issues in the prior art noted above.

BRIEF DESCRIPTION OF THE DRAWINGS

Various embodiments are shown and described in connection with the following drawings in which.

DETAILED DESCRIPTION

All references disclosed herein are hereby incorporated by reference in their entireties. In case of a conflict between the present disclosure and such references the present disclosure shall control.

Unless otherwise explained, all technical and scientific terms used herein have the same meaning as commonly understood by one of ordinary skill in the art to which this disclosure belongs. In case of conflict, the present specification, including explanations of terms, will control. The singular terms "a," "an," and "the" include plural referents unless context clearly indicates otherwise. Similarly, the word "or" is intended to include "and" unless the context clearly indicates otherwise. The term "comprising" means "including;" hence, "comprising A or B" means including A or B, as well as A and B together.

Although methods and materials similar or equivalent to those described herein can be used in the practice or testing of the present disclosure, suitable methods and materials are described herein. The disclosed materials, methods, and examples are illustrative only and not intended to be limiting.

Systems

Figure 1:
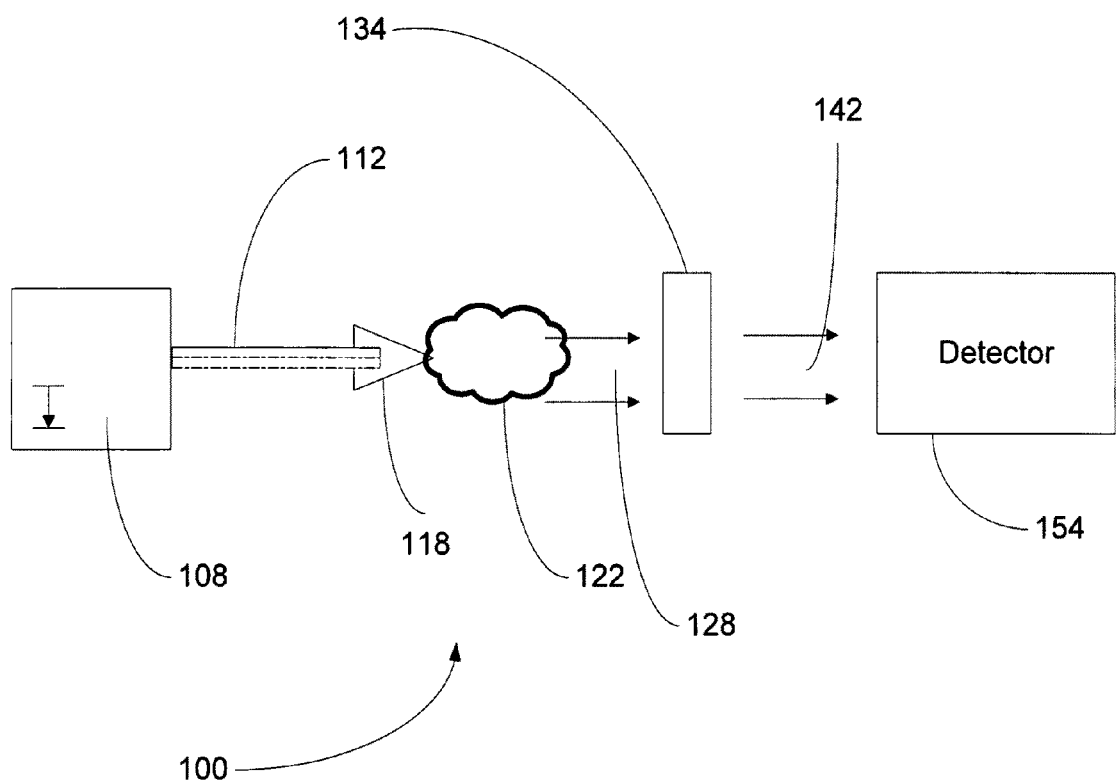
FIG. 1 is a schematic illustration of an embodiment imaging system according to the present disclosure.

FIG. 1 illustrates an embodiment of an imaging system 100 according to the present disclosure. The imaging system 100 includes a laser 108. The laser 108 generates a laser beam 112.

A target 118 is located in the path of the beam 112. In response to irradiation by the laser 108, the target 118 generates a laser produced plasma 122 and resulting radiation 128, such as k-alpha radiation.

A sample chamber 134 is placed in the path of the radiation 128. The properties of radiation 142 passing through or deflected by the sample 134 are recorded by a detector 154. In further embodiments, the sample chamber is omitted and the sample is placed in the path of the radiation 142.

The detector may be selected from any suitable recorder or measurer of x-rays, or signal produced therefrom, such as CCD cameras, streak cameras, pin hole cameras, x-ray image plates (such as phosphor plates), x-ray diodes, thermoluminescence detectors, germanium detectors, and scintillation detectors. The detector can include scintillation devices for generating signal for the detector 154. In a particular example, the image plates are Fuji ST-VA image plates and are read with the Fuji FCR-5000 image plate reader, available from FUJIFILM U.S.A., Inc., of Valhalla, N.Y.

The detector 154 is typically placed immediately after the sample when a conventional x-ray absorption image is desired. However, in some embodiments the detector 154 is placed suitably far from the sample such that Fresnel conditions (near-field diffraction) are obtained, which can provide information on both x-ray phase shift (the real component) and x-ray absorption (imaginary component). Obtaining both real and imaginary components can allow phase-contrast images of the sample to be obtained, which can provide more useful information than a conventional x-ray absorption image. Techniques for phase-contrast imaging are further described in Toth et al., "In-line Phase Contrast Imaging with a Laser-Based Hard X-ray Source" *Rev. Sci. Inst.* 76 083701-1, 6 (2005), incorporated by reference herein in its entirety.

The nature of the components used in the system 100 can vary based on the particular imaging technique used and the object to be imaged. In particular examples, the laser 108 has a power of 0.5-1000 TW, such as about 11 to about 20 TW. The operational parameters of the laser may also be adjusted based on the particular imaging technique and imaged object. For example, the energy delivered to the target 118 may depend on the material from which the target 118 is made, the thickness of the target 118, and the shape of the target 118. For example, target thickness can influence how quickly k-alpha radiation is produced and how long such radiation will be produced after the laser is switched off (afterglow radiation). Target thickness can also influence the amount of k-alpha radiation produced, as well as the composition of the produced radiation, generally.

Typically, the energy delivered to the target 118 is between about 10 mJ and 5000 mJ, such as about 10 mJ to about 1500 mJ. The pulse duration of the laser is typically from about 1 fs to about 1 ns. The peak energy delivered by the laser system is typically between about $10^{11}$ and $10^{20}$ W/cm$^2$, such as between about $10^{16}$ to about $10^{19}$ W/cm$^2$.

The focal spot size of the laser on the target can be selected based on the nature of the target 118 and the object to be imaged. The focal spot size can be empirically adjusted to optimize production of the desired radiation. Typical focal spot sizes may be in the µm range, such between about 1 and about 100 µm.

Suitable laser systems include CPA (chirped pulse amplification) lasers, such as TiSapp laser systems. A particular example of a TiSapp laser system useable in the systems and methods of the present disclosure is the 20 TW THOR laser of the University of Texas, Austin. Another TiSapp system useable in the systems and methods of the present disclosure is available at the Institute National de la Recherche Scientifque (IRNS) of the University of Quebec. Nd:glass lasers, such as that used at IRNS may also produce suitable plasmas. Details of a suitable Nd:glass laser system are described in Yu et al., *High Magnification Imaging with a Laser-Based Hard X-Ray Source* IEEE Journal of Selected Topics in Quantum Electronics, 5(4): 911-915 (July/August 1999), incorporated by reference herein in its entirety.

Radiation produced from the target may be focused or redirected toward the sample, such as using a spherically bent mica crystal, to redirect k-alpha radiation. In addition, filters can be used to tailor the radiation reaching the target or detector. For example, a filter may be used to reject radiation derived from sources other than the desired target material or above or below a certain energy threshold.

The system 100 can be used to produce k-alpha x-rays having an energy of between about 1 and 100 keV, such as between about 15 and about 74 keV. The energy of the x-rays can be tailored using a number of parameters, including the target material, target thickness, target shape, laser properties, and using various filters or other components. The energy of the x-rays is typically selected to provide maximum imaging capabilities while reducing patient radiation dose. For example, it may be useful to cut off radiation lower than about 15 KeV when the system is used for mammography. Higher energy radiation is typically used for thicker samples, such as keV for a 2.5 cm compressed breast and 21.5-25 keV for an 7 cm compressed breast.

In further implementations, the system 100 includes a target changer (not shown). The target changer automatically removes a spent target from the laser path and inserts a fresh target. The target changer can thus allow multiple radiation generating steps to occur in the course of a single imaging event or without manual intervention. Suitable target changers include rastered planes of targets, rotated disks of targets, or a tape or reel of targets. The target changer may be computer controlled in order to reduce interaction with the device, allow faster target changes, and allow more precise alignment with the laser 108.

Images obtained using the system 100 can provide a number of advantages as compared with conventional techniques. For example, radiation produced by the target 118 typically has a narrower (more monochromatic) energy profile than conventional x-rays tubes. The narrower profile can result in higher resolution imaging (since a greater flux of useful radiation is produced) and lower patient dose (since more of the radiation is in the range useful for imaging, not in that absorbed by tissue, for example).

Target Types and Fabrication

The methods of the present disclosure typically use targets containing a metal layer and which define a hollow inner surface. The hollow inner surface has an internal apex, which, in some examples, is less than about 15 µm between two opposing points of the internal apex.

Figure 2:
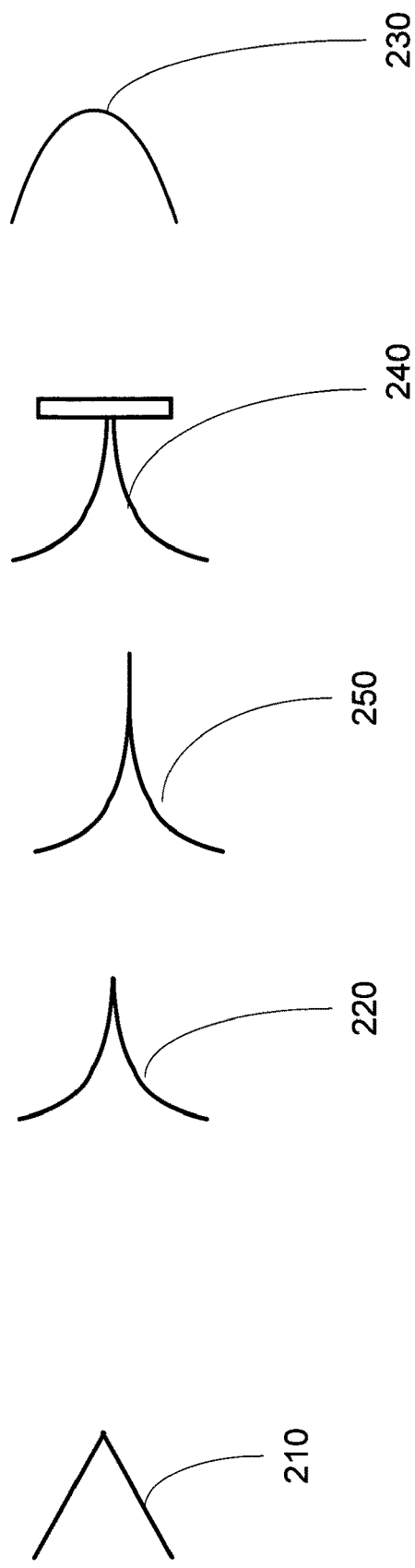
FIG. 2 illustrates examples of target shapes that can be used in the systems and methods of the present disclosure, such as the system of FIG. 1.

Although many target shapes can be used, FIG. 2 illustrates several examples of target shapes. The targets can be, for example, pyramidal 210, conical 220, or hemispherical 230. In yet further examples, a cap of material extends perpendicularly from the apex, such as target 240, a conical target with a cap. The cap may be made from one or more materials, including metals which may be the same or different from the metal layer of the target.

The targets may also have an embedded wire or fluor, such as target 250, a conical target with an embedded wire. Targets with caps, wires, additional exterior layers, and fluors are discussed further below. When capped targets are used for imaging, it may be useful to place a particle absorbing barrier between the imaged object, such as a patient, and the target in order to prevent or reduce the objects contact with any particles created by irradiation of the target.

Suitable targets and methods for their fabrication are disclosed in PCT/US2006/035267, incorporated by reference herein in its entirety. Certain techniques described in that application produce hollow targets. Targets with embedded fluors can be created by depositing one or more fluor materials, such as one or more metals, into the hollow interior of the target, such as by e-beam or thermal evaporation, sputtering or electroplating techniques. Standard photolithography techniques are used, in some examples, to help control the shape and degree of deposition of the fluor material. Such techniques may also be used to deposit a layer of radiation enhancing material on an exterior surface of a target, such as in the area of the target apex.

Plasma Production by Targets

Figures 3A, 3B:
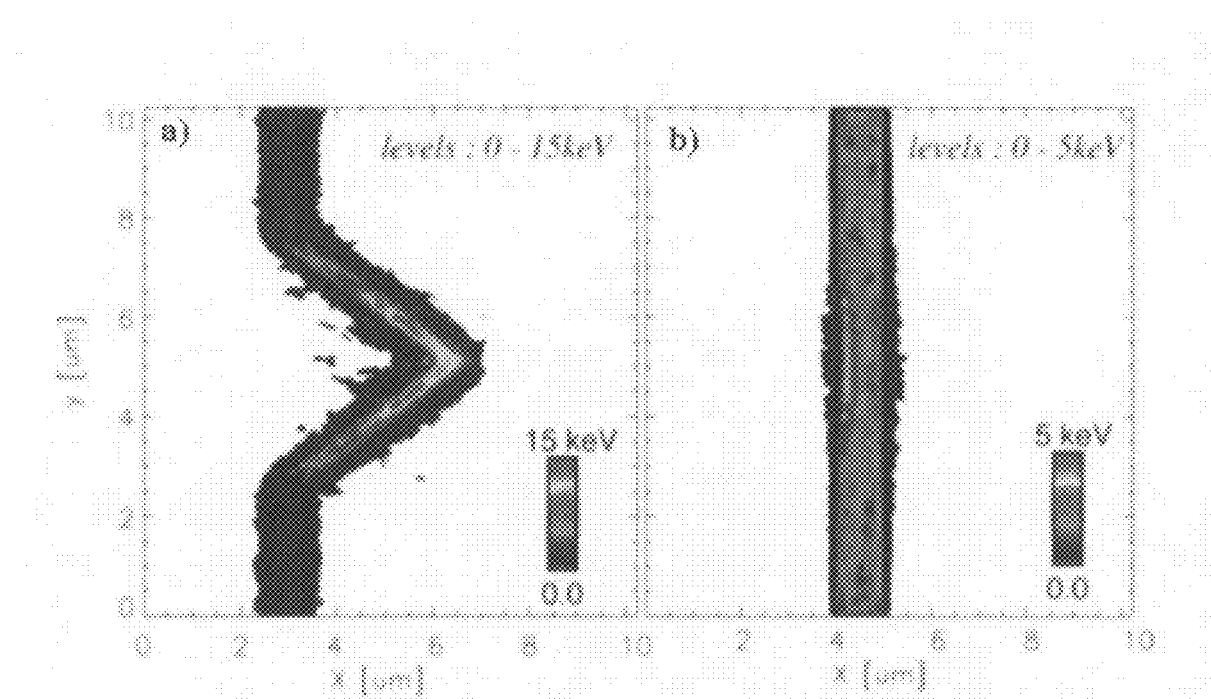
FIGS. 3(a) and 3(b) are graphs illustrating: (a) hot electron energy of cone verses; (b) a flat foil after 200 fs with p polarization.

FIG. 3 shows spatially resolved PIC simulations of the electron energy found with a gold cone target (3(*b*)) versus a flat gold foil target (3(*b*)) shot at 0° at 200 fs. The simulation of the flat foil indicated very few spots on the foil with energies approaching even 5 keV. In contrast, the simulations of the cone illustrate large portions of the cone, particularly towards the tip, having energies of up to 15 keV.

Figure 4A:
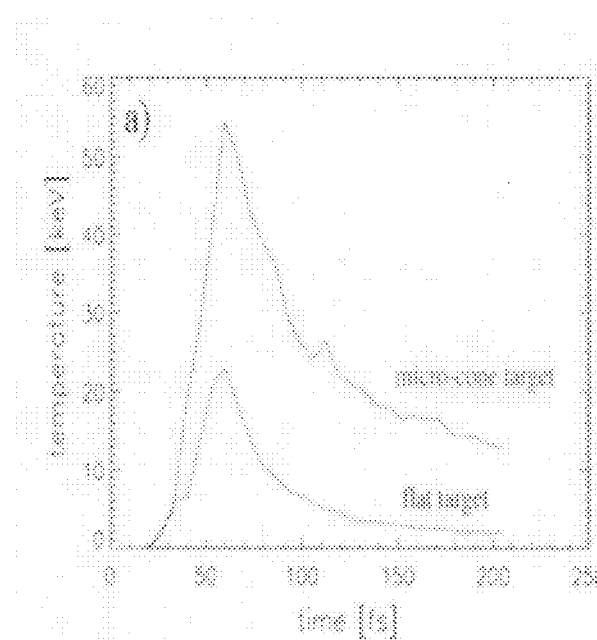
FIG. 4(a) illustrates the electron temperature plot for electrons in the target material for cone versus flat foil targets.
Figure 4B:
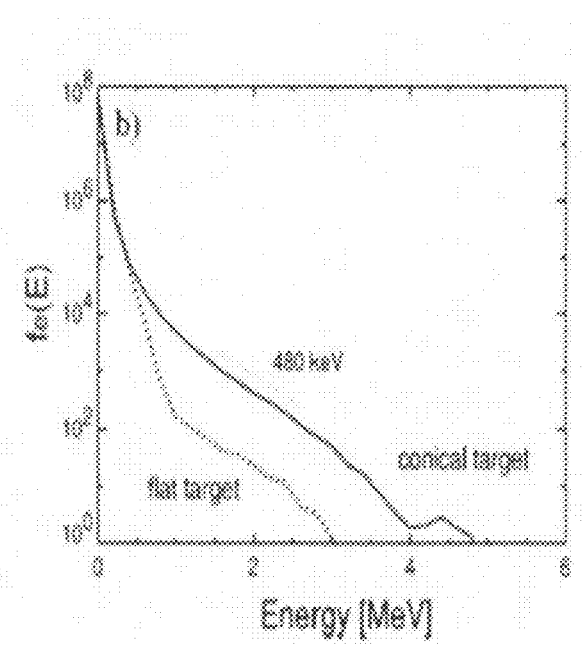
FIG. 4(b) illustrates how a conical target geometry can increase electron energy and electron density.

The corresponding time resolved hot electron temperature for the cone and foil targets is demonstrated in FIG. 4(*a*) while the augmented hot electron density is shown in FIG. 4(*b*). While the conical target produced electrons having energies of about 55 keV, the maximum energy produced by the foil was about 2 keV. Similarly, the energy density of the conical target shows a larger population of energetic electrons compared with the flat foil, the conical electrons having an average energy of about 480 keV.

Figures 5A, 5B, 5C:
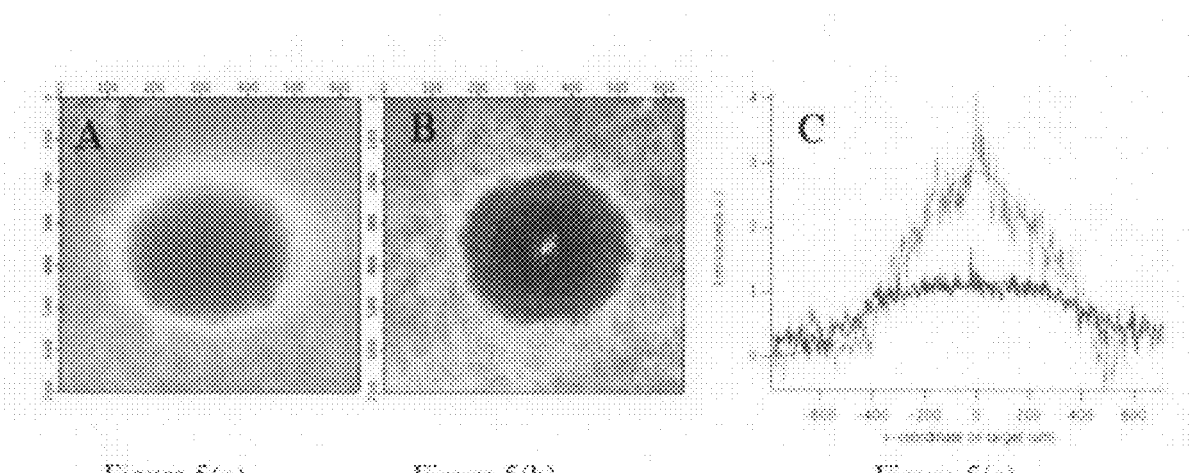
FIGS. 5(a)-(c) are graphs illustrating X-ray emission from 5(a) thin Au foil; 5(b) pyramid; 5(c) lineouts of 5(a) versus 5(b).

Conical targets consisting of ten micron thick gold formed into free-standing pyramids have been built and studied with the THOR laser at the University of Texas at Austin (Ti-Sapph laser, irradiance $1 \cdot 10^{19}$ W/cm$^2$, 400 mJ, pulse length 40 fs, focal spot size 10 µm). Results from these targets are shown in FIG. 5. These images were taken with a pinhole camera from both a flat and pyramidal gold target.

As shown in FIGS. 5(*a*) and 5(*b*), showing x-ray emission from the targets, pyramidal targets produced more intense x-ray emission towards the target apex. The results show an approximate three-fold enhancement in X-ray yield with the pyramidal targets. The lineout of FIGS. 5(*a*) and 5(*b*), illustrated in FIG. 5(*c*), show a 2.8 fold increase in intensity and a two-fold decrease in source size for the pyramidal geometry versus the flat foil, confirming that the pyramidal geometry increases x-ray intensity and decreases source size. Perpendicular emission of particles can help reduce or eliminate particles in the X-ray beam. As described below, cleaner, brighter, quasi-monochromatic X-ray sources may find use in many imaging techniques, including various medical diagnostic regimes.

Figures 6A, 6B:
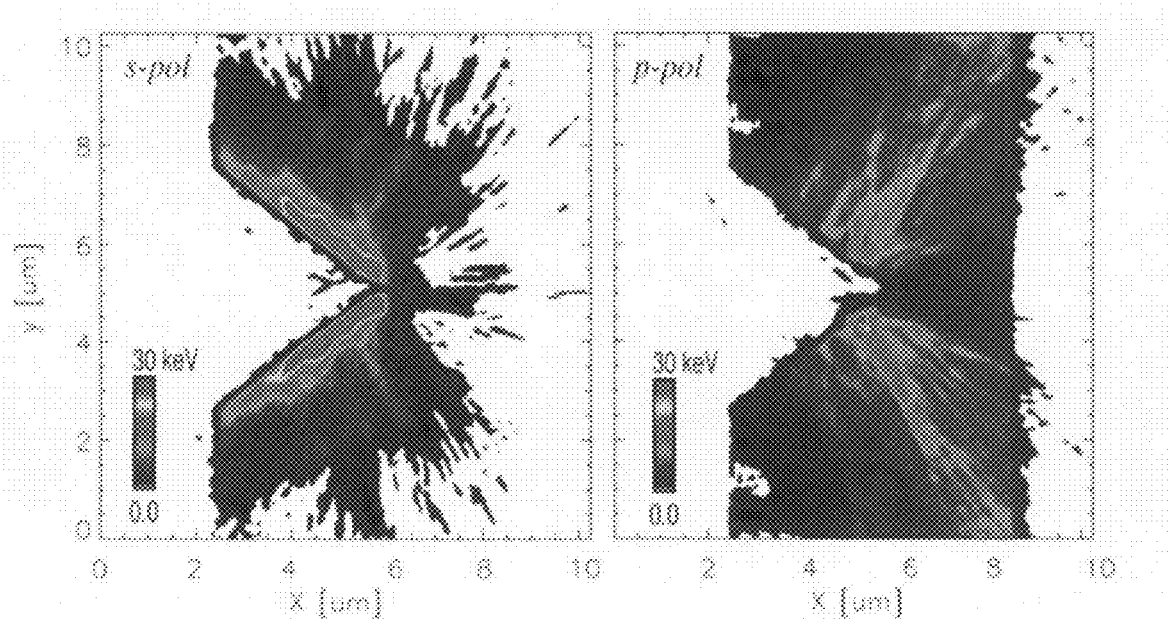
FIGS. 6(a) and (b) illustrate, respectively, simulated electron emission from pyramidal targets using s and p polarized lasers.

In some cases, such as with unsymmetrical targets, energy or x-ray emission can be enhanced using a polarized laser. For example, FIG. 6 illustrates simulated electron emission from wedge targets using s (6(*a*)) and p (6(*b*)) polarized lasers. Much more energetic electrons result using the s polarized case, which apparently heats up more of the target surface. However, energetic electrons are emitted from the pyramid tip using the p-polarized laser.

Imaging Methods

Figure 7:
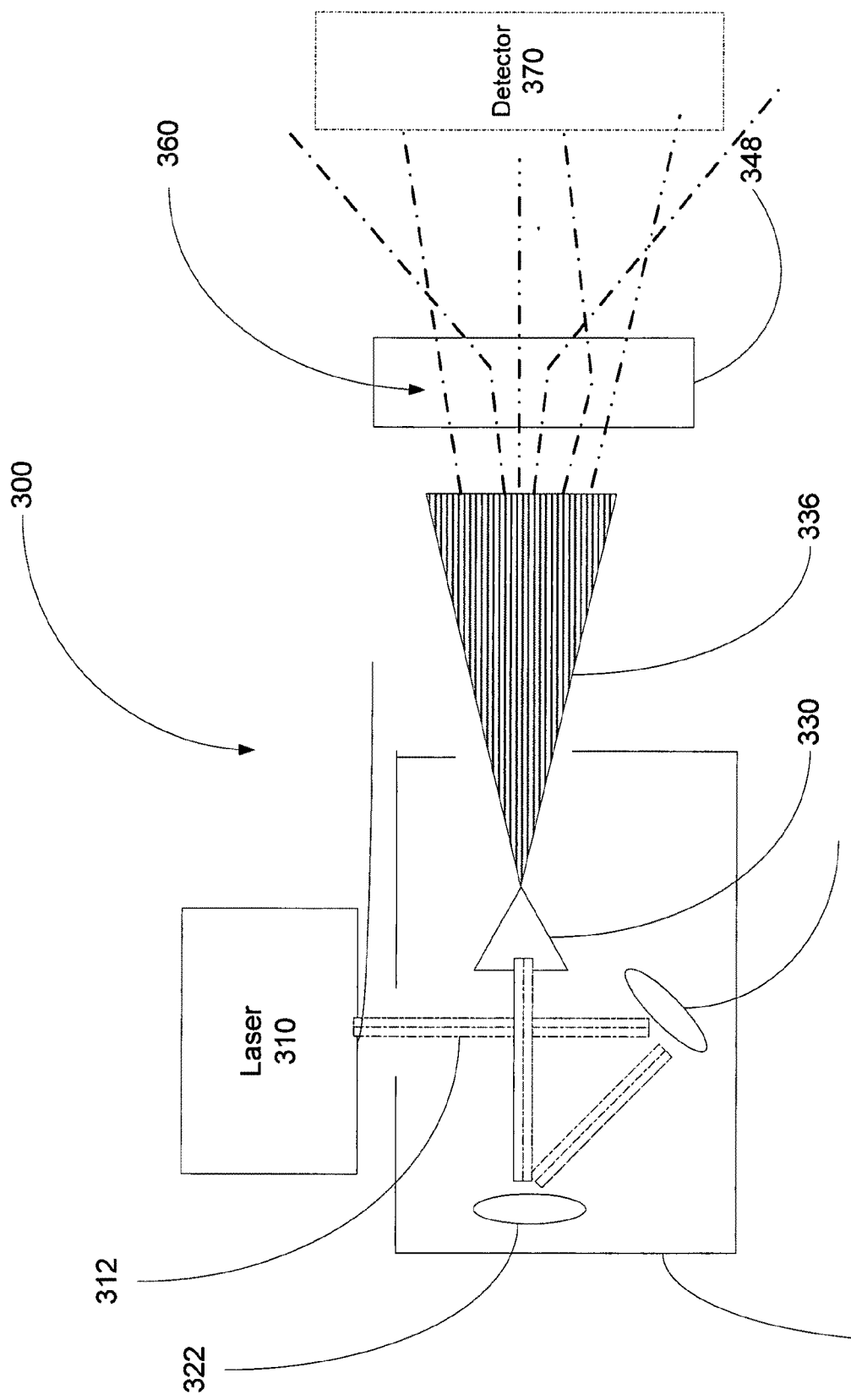
FIG. 7 is a schematic diagram illustrating a system according to the present disclosure useable for time-gated x-ray tomography.

FIG. 7 presents a system 300 for use in certain imaging techniques, such as time-gated x-ray tomography. The system 300 includes a laser 310, which may be selected as discussed for the laser 108 of FIG. 1. The beam 312 from the laser 310 enters a vacuum chamber 314 where it is redirected using mirrors 318, 322. The redirected beam 312 strikes the target 330, which may be selected as described for the target 118 of FIG. 1.

Radiation 336, such as k-alpha x-rays, is generated by the target 330 and passes through the sample (imaged object) 348. It can be seen that a portion of the radiation 360 is scattered by the sample 348. At least a portion of the radiation 360 enters the detector 370 where it is measured and recorded. The detector 370 may be selected as described for the detector 154 of FIG. 1. In particular embodiments, the detector 370 includes a streak camera, such as a Kentech x-ray streak camera, available from Kentech Instruments Ltd., of Wallingford, Oxfordshire, UK. Pinhole cameras or CCD cameras may also be used as the detector 370. One suitable CCD camera is the PI-SCX camera, available from Princeton Instruments of Trenton, N.J. The camera may be coupled to a suitable scintillator, such as a $Gd_2SO_2$ scintillator.

In certain time-gated techniques, the sample 348 is rotated and the detector 370 is synchronized with the sample rotation in order to produce a time-gated signal. In particular embodiments, the detector 370 is a two-dimensional time-gated detector, allowing the entire volume of the sample 348 to be imaged. Time-gated imaging is discussed further in Grätz et al., "Time-gated X-ray Tomography" *App. Phys. Lett.* 73(20) 2899-2901 (1998), incorporated by reference herein in its entirety.

Mammography

Figure 8:
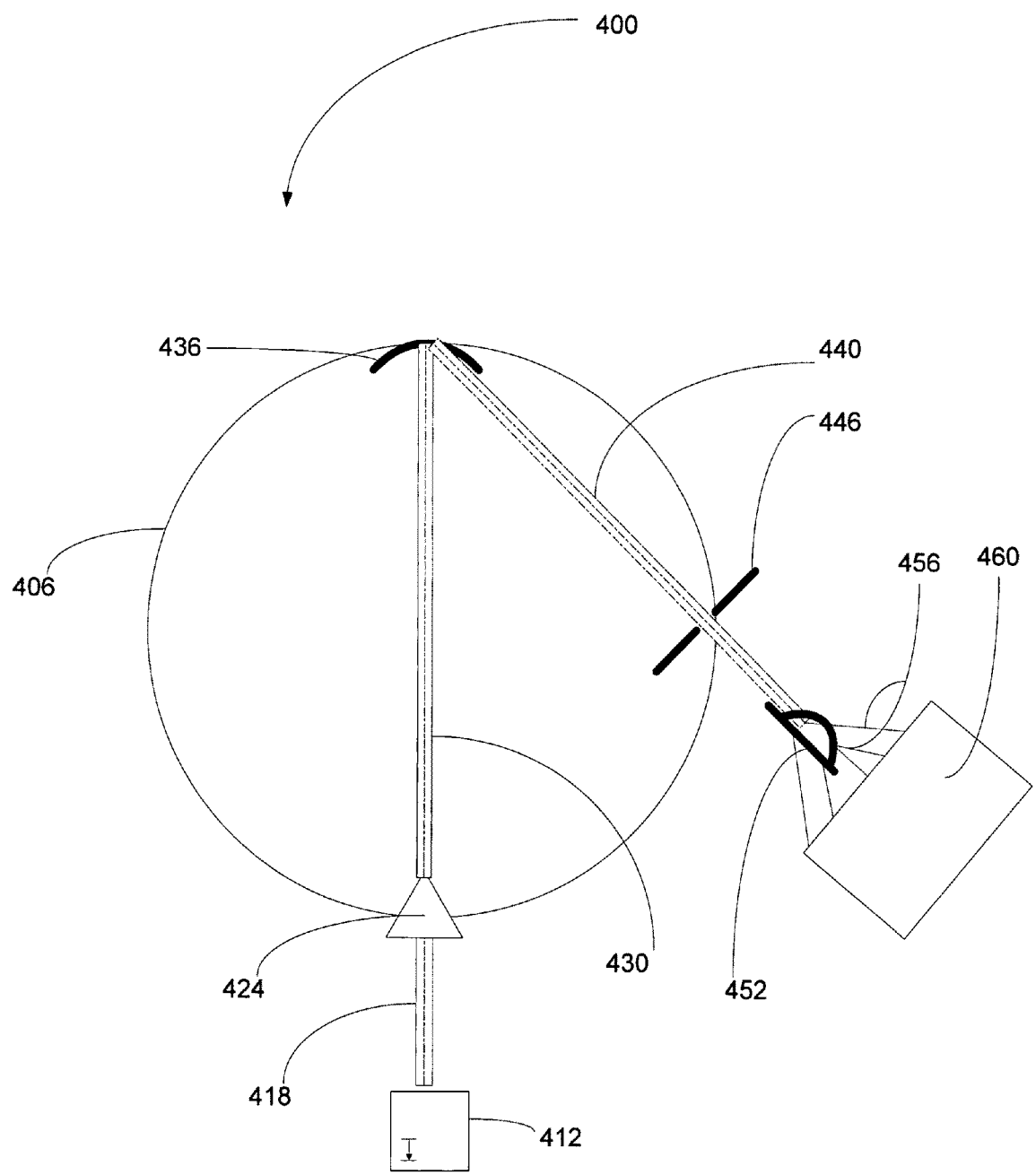
FIG. 8 is a schematic diagram illustrating a system according to the present disclosure useable for mammography.

FIG. 8 presents an imaging system 400 that can be used to image a subject, such as for mammography. Unless otherwise specified, components of the system 400 can be selected as described for the system 100 of FIG. 1.

The system 400 is set up using a Rowland circle 406. In a particular implementation, the Rowland circle 406 has a radius of about 1 m. A laser 412 produces a beam 418. The beam 418 impacts a target 424 located on the circumference of the Roland circle 406. The target 424 produces a stream of radiation 430, which typically includes K-alpha radiation.

The stream of radiation 430 contacts a deflection/selection device 436 which redirects and, optionally, filters the radiation 430. The deflection/selection device 436 may be, for example, a spherically bent monochromator. The monochromator can be used to select a particular energy, or energy range, of the radiation 430. For example, the monochromator can be used to select an energy range, such as 0.02-1 KeV, of X-rays likely to have most utility in imaging an object. In at least some embodiments the monochromator is tunable and can be adjusted to provide different radiation energies depending on the object to be imaged.

The deflected radiation stream 440 passes out of the Roland circle 406 through an exit slit 446. The exit slit 446, along with the deflection device 436, can be used to determine the focal size and point of the deflected radiation stream 440. After exiting the Roland circle 406, the deflected radiation sample passes through at least a portion of the subject (imaged object) 452, such as a breast in mammography. Radiation 456 passing through the subject 452 is measured by a detector 460.

Targets with an Embedded Fluor, Wire, or Cap

The targets, in some implementations, include a radiation generating component, such as a wire, which may extend from the apex of the target, an embedded fluor, a layer on an exterior surface of the target, or a cap, such as a cap perpendicular to the apex of the target. In some examples, a fluor material is embedded or otherwise placed at the focal point of a target, such as in the tip of a cone.

The fluor, wire, exterior layer, or cap can act as a source of radiation, such as X-rays. In a particular example, the material is chosen according to the preferred K-alpha energy desired for a particular application. For elemental materials, K-alpha energy is generally related to the atomic number (Z), elements having a higher atomic number having more energetic K-alpha radiation. Some suitable materials for radiation generating moieties, their atomic numbers, and K-alpha energies are listed in the following table.

| Element | Mo | Ce | Gd | Ta | W | Au |
|---|---|---|---|---|---|---|
| Atomic Number | 42 | 55 | 64 | 73 | 74 | 79 |
| K-Alpha energy (keV) | 17.48 | 30.97 | 42.98 | 57.52 | 59.31 | 68.78 |

When the radiation enhancing material is located towards the tip of a target, an incoming laser beam can interact with the inside tip of the target and can help prevent or reduce early heating of the radiation enhancing material. Suprathermal electrons driven forward via large electric and magnetic fields penetrate the cold material to produce K-alpha X-rays.

Figure 9A:
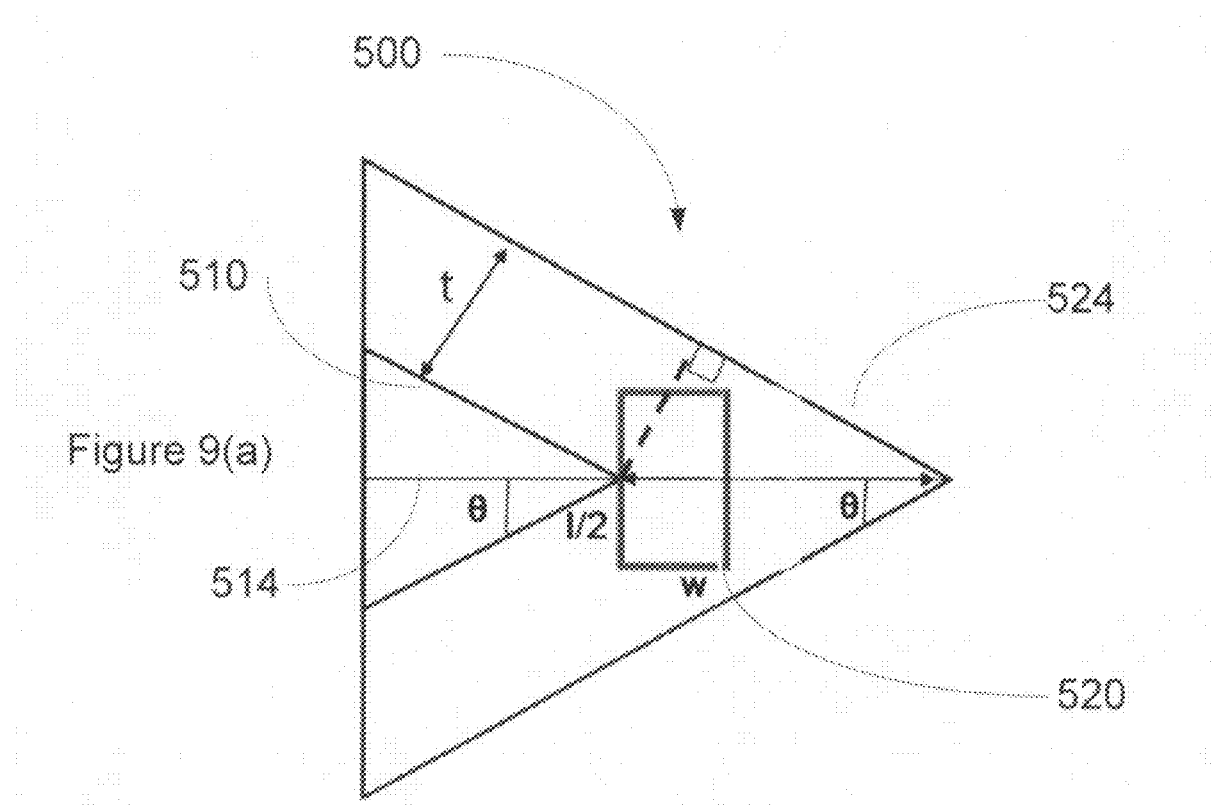
FIGS. 9(a) and 9(b) are, respectively, top and side cross sectional views of a target having an embedded fluor material.

FIG. 9(a) illustrates a top cross sectional view of a pyramidal or conical target 500. The target 500 has a width t and the inner surface 510 forms an angle θ with respect to the axis 514 of the target 500. In particular implementations, θ is 35°. The target 500 has a length l. A fluor 520 is disposed within the tip 524 of the target 500. In at least some embodiments, the fluor 520 is located slightly apart from the inner surface 510 proximate the tip 524. Proper location of the fluor 520 can help maximize radiation enhancement. In particular examples, optimal fluor placement is empirically determined.

In some configurations, the width of the fluor, w, is between about 1 μm about t/sin θ μm. In further implementations, the width w of the fluor and the target length is given by:

$$w=(2t-1\cos\theta)/(2\sin\theta)$$

or $$1=(2t-2w\sin\theta)/(\cos\theta)$$

Figure 9B:
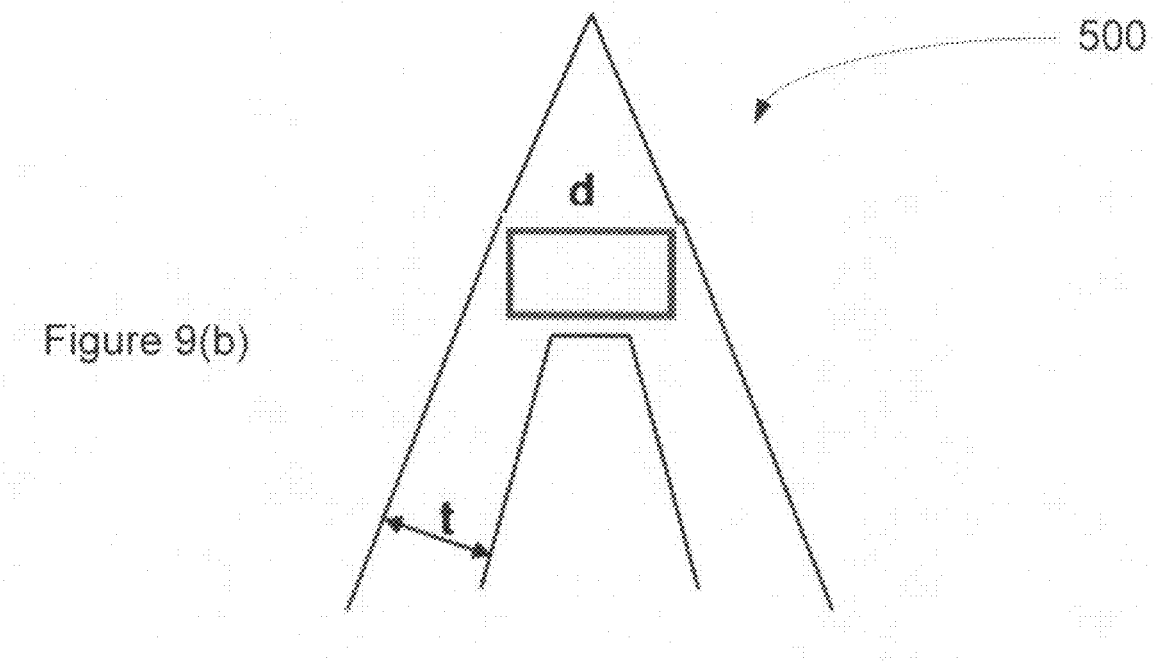

FIG. 9(b) illustrates a side cross sectional view of the target 500. The target has a depth d, typically between about 1 μm and about 10 μm.

Figure 10:
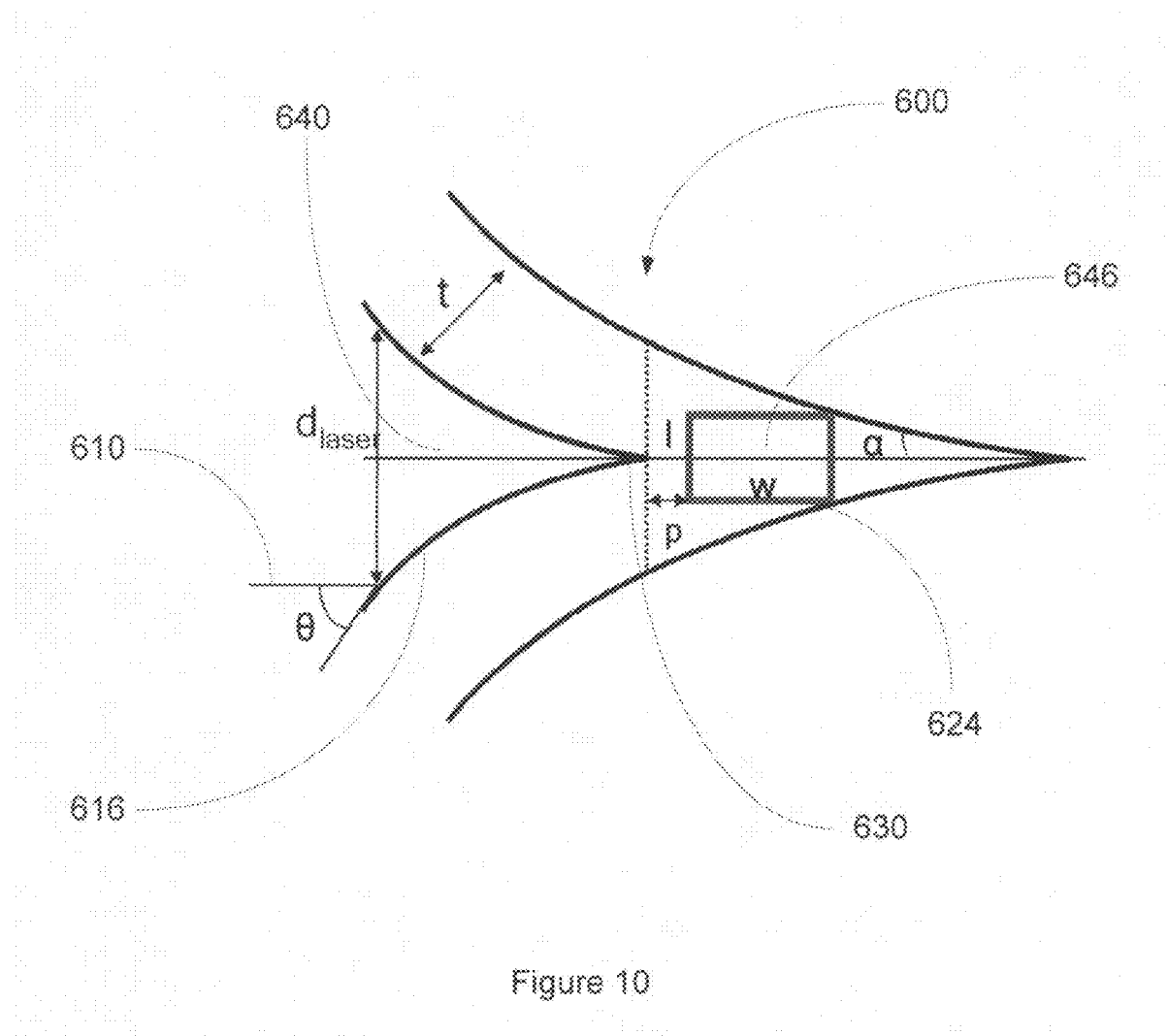
FIG. 10 is a side cross sectional view of a target having an embedded fluor.

FIG. 10 illustrates a side cross sectional view of a target 600, which may be a conical target. The target 600 has a diameter d, a length l, and a thickness t. A tangent 610 to the inner surface 616 of the target 600 defines an angle θ. In some instances, θ is 35.5°.

A fluor 624 is located within the target 600. The fluor has a width w and is located a distance p from the tip 630 of the inner target surface. The axis 640 of the target 600 defines an angle a with respect to the outer surface 646 of the target 600. In some instances, a is between about 44° and about 87°.

In some examples, the width range of the fluor is between 1-p μm and t/sin(a-p) μm. In further examples, the length and width are related by:

$$w=(2t-1\cos\alpha)/(2\sin\alpha)+p$$

or $$1=(2t-2(w-p)\sin\alpha)/(\cos\alpha)$$

In addition to potentially enhancing x-ray yield, radiation enhancing moieties may also allow for irradiation of a sample with multiple types of radiation, such as from the target itself and one or more radiation enhancing components. Using multiple types of energy can, in some methods, allow higher quality images to be obtained through the use of image algebra, such as image subtraction. The image contrast can be further enhanced, in some embodiments, by treating the imaged object with a radiosensitive material, such as administering a radiosensitive agent to a subject.

Medical Applications

An attractive feature of LPP X-ray sources is the small source size typically obtained from LPP sources, which can allow for higher magnification and improved resolution of smaller objects. Therefore, detection of small calcifications not currently detectable via a standard mammography unit, for example, could become standard practice.

LPP X-ray sources also typically have short emission duration, allowing for image gating. Gating typically allows only ballistic photons to reach the detector while slower scattered photons contributing to image blur are eliminated or reduced.

LPP sources can enhance line emission over the bremsstrahlung continuum. Thus, it is possible to minimize patient dose while forming a sharper image. In some specific techniques, two radiation enhancing materials (such as fluors, caps, or wires) are chosen having energy profiles that bridge the K-edge of a radiosensitive agent administered to a subject.

Backlighting Applications

The systems of the present disclosure can also be adapted for backlighting applications. Backlighting techniques are described in Landen et al., "X-ray Backlighting for the National Ignition Facility," *Rev. Sci. Inst.* 72(1)627-634 (2001), incorporated by reference herein in its entirety. The present systems can be adapted for various backlighting techniques, including area backlighting, point projection backlighting using point targets, and point projection backlighting using pinholes.

In more specific implementations, a radiation enhancing component of the target and a target layer are used to produce polychromatic backlighting. In further implementations, the targets provide polychromatic backlighting through multiple radiation enhancing components, such as one or more embedded fluors, exterior layers, wires, or caps.

The target and/or radiation enhancing components can be selected to provide radiation having desired characteristics. For example, appropriate selection of target and/or components can produce distributed or spectrally broader photon flux. Enhanced photon flux can allow for spectrally brighter backlighting. For example, the target and/or radiation enhancing components may include two or more of V, Ti, and Sc or two or more of Ag, Rh, and Mo.

Compared to existing polychromatic backlighters, the targets, systems, and methods of the present disclosure can provide various advantages. For example, targets can be produced where all of the backlight radiation generating components are on a single target. In further examples, the targets allow a single laser to be used to irradiate the various backlighting sources, which can expand the range of systems useable for such methods, reduce system complexity, and cost. This can be advantageous compared to at least certain polychromatic backlighting techniques which generally required facilities with many laser beams in order to irradiate all of the system components necessary for the imaging technique.

EXAMPLE 1

Mammography

A mammography imaging system is set up generally as shown in FIG. 8. The laser is a Ti-Sapph laser having an irradiance of $1 \cdot 10^{19}$ W/cm$^2$, 400 mJ, and a pulse length of 40 fs. The focal spot size is 10 µm. The target is a gold coated, free-standing cone having an internal apex of less than about 1 µm. The thickness of the gold coating is about 10 µm. The target is selected, and the imaging system components selected, to produce k-alpha radiation having energies in the range of 15-25 keV.

The focal point of the x-ray beam exiting the exit aperture is determined. An x-ray transparent plate is mounted at the focal point of the x-ray beam. In a particular example, a Fuji ST-VA image plate is placed in line with the transparent plate.

A breast of a patient is exposed and compressed against the x-ray transparent plate. The target is irradiated with the laser. The plate is read using a Fuji FCR-5000 image plate reader. The resulting image is assessed in order to diagnose the condition of the patient.

EXAMPLE 2

Phase Contrast Imaging of a Mouse

A phase contrast imaging system is set up generally as shown in FIG. 1. The laser is a Ti-Sapph laser having an irradiance of $1 \cdot 10^{19}$ W/cm$^2$, 400 mJ, and a pulse length of 40 fs. The focal spot size is 10 µm. The target is a gold coated, free-standing cone having an internal apex of less than about 1 µm. The thickness of the gold coating is about 10 µm. The target is selected, and the imaging system components selected, to produce k-alpha radiation having energies in the range of 10-20 keV. The detector is a PI-SCX CCD camera (Princeton Instruments, Trenton, N.J.) coupled to a $Gd_2SO_2$ scintillator optimized for radiation having energies of 10-20 keV.

The focal point of the x-ray beam exiting the target is determined. The mouse is placed at the focal point of the x-ray beam. The distance between the mouse and the CCD camera is 90 cm.

The mouse is irradiated with the laser and x-ray phase shift and x-ray absorption are measured. The resulting images are recorded using the CCD camera.

EXAMPLE 3

Time-Gated Imaging of a Mouse

An imaging system is set up generally as shown in FIG. 1. The laser is a Ti-Sapph laser having an irradiance of $1 \cdot 10^{19}$ W/cm$^2$, 400 mJ, and a pulse length of 40 fs. The focal spot size is 10 µm. The target is a gold coated, free-standing cone having an internal apex of less than about 1 µm. The thickness of the gold coating is about 10 µm. The target is selected, and the imaging system components selected, to produce k-alpha radiation having energies in the range of 10-25 keV. The detector is a Kentech x-ray streak camera with a time resolution of about 50 ps read out using a La Vision FlameStar IIF CCD camera (LaVision, Inc., Ypsilanti, Mich.), as described in Gratz et al., *IEEE J. Sel. Top. Quantum Electron.* 2, 1041 (1996), incorporated by reference herein in its entirety.

The flux of x-rays in the x-ray beam exiting the target is determined. The mouse is placed in a rotating cage at an appropriate point in the x-ray beam. The detector is placed directly behind (10 cm) the mouse, in line with the target.

The mouse cage is rotated through 180°. The target is irradiated with the laser, and images recorded at 5° intervals using a gate having a width of 45 ps, centered 15 ps before the maximum of the unscattered peak. The images are normalized and backprojected as described in *Technical Aspects of Computed Tomography*, T. H. Newton and D. G. Potts, Eds., (Mosby, 1981), incorporated by reference herein in its entirety to produce a time-gated image of the mouse.

It is to be understood that the above discussion provides a detailed description of various embodiments. The above descriptions will enable those skilled in the art to make many departures from the particular examples described above to provide apparatuses constructed in accordance with the present disclosure. The embodiments are illustrative, and not intended to limit the scope of the present disclosure. The scope of the present disclosure is rather to be determined by the scope of the claims as issued and equivalents thereto.

We claim:

1. An imaging system comprising:
   a laser;
   a hollow target placeable in electromagnetic communication with the laser, the hollow target comprising a first end and a second end and a metal layer defining an aperture at the first end, the metal layer further defining an internal apex and an external apex at the second end, the internal and external apexes being opposite the aperture, the internal apex comprising two opposing points separated by a distance of less than about 15 µm; and
   a detector in electromagnetic communication with the hollow target.

2. The imaging system of claim 1 wherein the target is cone shaped.

3. The imaging system of claim 1 wherein the target is pyramidal.

4. The imaging system of claim 1 wherein the target is hemispherical.

5. The imaging system of claim 1 wherein the target comprises a radiation enhancing component selected from an embedded fluor, a wire, or a cap.

6. The method of claim 5, wherein the radiation enhancing component is located proximate the focal point of the target.

7. The imaging system of claim 1 further comprising a target changer, the target being one of a plurality of targets mounted in the target chamber.

8. The imaging system of claim 1, wherein the target has an internal apex of less than about 1 µm.

9. An imaging method comprising:
   providing a hollow target comprising a first end and a second end and a metal layer defining an aperture at the first end, the metal layer further defining an internal apex and an external apex at the second end, the internal and external apexes being opposite the aperture, the internal apex comprising two opposing points separated by a distance of less than about 15 µm;
   irradiating the target with a laser, the irradiation of the target producing a beam of radiation comprising k-alpha x-rays;
   passing the beam of radiation through a subject;

detecting at least a portion of the radiation passing through the subject; and generating an image of the subject.

10. The method of claim 9, further comprising diagnosing a condition of the subject based on the image.

11. The method of claim 9, further comprising rotating the subject and synchronizing the detector with the sample rotation, thus providing a time gated signal.

12. The method of claim 9 further comprising, wherein the target is a first target and, after irradiating the target, moving the first target out of electromagnetic communication with the laser and placing a second target in electromagnetic communication with the laser.

13. The method of claim 9, further comprising positioning the detector from the subject such that Fresnel conditions are obtained.

14. The method of claim 13, further comprising detecting real and imaging components of x-ray transmission and producing a phase-contrast image of the subject.

15. The method of claim 9, further comprising administering a radiosensitive agent to the subject.

16. The method of claim 15, further comprising irradiating the subject with radiation that bridges the K-edge of the radiosensitive agent.

17. The method of claim 9, wherein the target comprises a radiation enhancing component, further comprising selecting the radiation enhancing component to produce radiation suitable for imaging the subject.

18. The method of claim 9, wherein the internal apex of the target is less than about 1 μm.

19. The method of claim 9, further comprising focusing the laser towards the apex of the target using the internal target surface.

20. An imaging system comprising:

a laser;

a hollow target placeable in electromagnetic communication with the laser, the hollow target comprising a first end and a second end and a metal layer defining an aperture at the first end, the metal layer further defining an internal apex and an external apex at the second end, the internal and external apexes being opposite the aperture, the internal apex comprising two opposing points separated by a distance of less than about 15 μm;

a radiation enhancing component coupled to the target; and a detector in electromagnetic communication with the hollow target.

* * * * *